(12) United States Patent
Nagano et al.

(10) Patent No.: US 8,461,358 B2
(45) Date of Patent: Jun. 11, 2013

(54) FLUORESCENT PROBE FOR MEASURING PROTEASE

(75) Inventors: Tetsuo Nagano, Tokyo (JP); Yasuteru Urano, Kanagawa (JP); Masayo Sakabe, Tokyo (JP)

(73) Assignee: The University of Tokyo, Toyko (JP)

( * ) Notice: Subject to any disclaimer, the term of this patent is extended or adjusted under 35 U.S.C. 154(b) by 0 days.

(21) Appl. No.: 13/201,537

(22) PCT Filed: Feb. 19, 2010

(86) PCT No.: PCT/JP2010/001077
§ 371 (c)(1),
(2), (4) Date: Oct. 27, 2011

(87) PCT Pub. No.: WO2010/095450
PCT Pub. Date: Aug. 26, 2010

(65) Prior Publication Data
US 2012/0052518 A1    Mar. 1, 2012

(30) Foreign Application Priority Data

Feb. 20, 2009 (JP) .................................. 2009-037284

(51) Int. Cl.
*C07D 313/00* (2006.01)
*A61K 39/00* (2006.01)

(52) U.S. Cl.
USPC ........................................... 549/344; 435/15

(58) Field of Classification Search
USPC ........................................... 549/344; 435/15
See application file for complete search history.

(56) References Cited

U.S. PATENT DOCUMENTS

| | | | |
|---|---|---|---|
| 4,557,862 A | 12/1985 | Mnagel et al. |
| 6,201,134 B1 | 3/2001 | Nagano et al. |
| 6,346,373 B1 | 2/2002 | Mancini et al. |
| 6,441,197 B1 | 8/2002 | Nagano et al. |
| 6,469,051 B2 | 10/2002 | Nagano et al. |
| 6,756,231 B1 | 6/2004 | Nagano et al. |

FOREIGN PATENT DOCUMENTS

| | | |
|---|---|---|
| WO | 00/68414 | 11/2000 |
| WO | 2011087000 | 7/2011 |

OTHER PUBLICATIONS

Leytus et al., "New class of sensitive and selective fluorogenic substrates for serine proteinases", Biochemical Journal, 1983, Nagano et al., vol. 215, No. pp. 253-260.
Leytus et al., "Rhodamine-based compounds as fluorogenic substrates for serine proteinases", Biochemical Journal, 1983, vol. 209, No. 2, pp. 299-307.
Lorey et al., "Transcellular Proteolysis Demonstrated by Novel Cell Surface-associated Substrates of Dipeptidyl Peptidase IV (DC26)*", Journal of Biological Chemistry, 2002, vol. 277, No. 36, pp. 33170-33177.
Steven et al., "Further inhibition studies on Guanidinobenzoatase, a Trypsin-like Enzyme Associated with Tumor Cells", Journal of Enzyme Inhibition, 1987, vol. 1, No. 3, pp. 187-201.
"Chemical Abstracts", Chemical Substance Index, 2006, vol. 144, 28564CS-28565CS.
English and Japanese versions of the International Preliminary Report on Patentability and Written Opinion for International Application PCT/JP2010/001077, mailed Sep. 22, 2011.
English and Japanese versions of the International Search Report for International Application PCT/JP2010/001077, mailed Mar. 23, 2010.

*Primary Examiner* — Nizal Chandrakumar
(74) *Attorney, Agent, or Firm* — Greenblum & Bernstein, P.L.C.

(57) ABSTRACT

A compound represented by the formula (I) or a salt thereof ($R^1$ represents hydrogen atom, or a substituent; $R^2$ to $R^7$ represent hydrogen atom, hydroxyl group, an alkyl group, or a halogen atom; $R^8$ and $R^9$ represent hydrogen atom, or an alkyl group; X represents a $C_1$-$C_3$ alkylene group; and $R^{10}$ represents an acyl group), which promptly causes a structural change from a non-fluorescent closed ring structure to a strongly fluorescent open ring structure by hydrolysis of an acyl group, and is useful as a fluorescent probe for measuring a protease showing superior suitability for quantification.

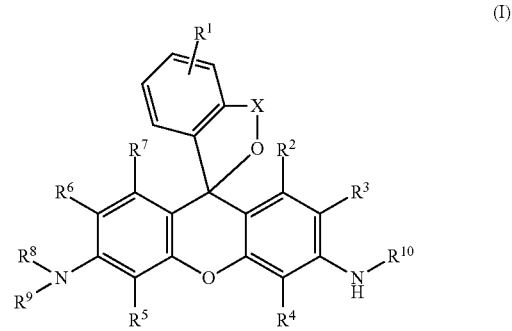

6 Claims, 2 Drawing Sheets

FLUORESCENT PROBE FOR MEASURING PROTEASE

TECHNICAL FIELD

The present invention relates to a fluorescent probe for measuring a protease.

BACKGROUND ART

Fluorescent probes are functional molecules which are substantially non° fluorescent in the absence of a target substance, and become fluorescent after a reaction with the target substance. Since fluorescent probes achieve measurement of a target substance at an extremely low concentration under mild conditions such as neutral pH and physiological temperature, and enable highly sensitive imaging of a target substance existing in living tissues or organs, they are widely applied as probes for measurement of nitric oxide, reactive oxygen species, metal ions, and the like. As fluorescent probes for measuring a protease, the following probes have been proposed (Biochemical Journal, 201, pp. 367-372, 1982).

Xanthene dyes such as fluorescein and rhodamine are used as fundamental skeletons of fluorescent probes. Xanthene dyes are strongly fluorescent when they have an open ring structure. Whilst, when they have a closed ring structure in which a lactone ring is formed, the conjugation of the fluorophore is cleaved, and therefore they are substantially nonfluorescent. For applying this phenomenon to off/on control of fluorescence, fluorescent probes have been designed which react with a target substance so that structural change from the closed ring structure to the open ring structure is induced.

For example, the following diacyl type fluorescent probe for measuring a protease using the rhodamine structure is known. This diacyl type fluorescent probe becomes a weakly fluorescent compound having an open ring structure due to hydrolysis of the acyl group at one side by a protease, and when the other acyl group is further hydrolyzed, strongly fluorescent diaminorhodamine is generated (Biochemistry, 38, pp. 13906-13911, 1999).

[Formula 1]

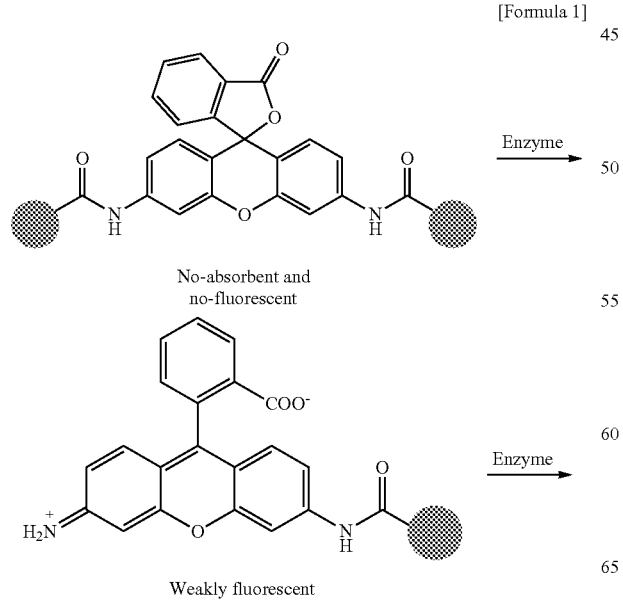

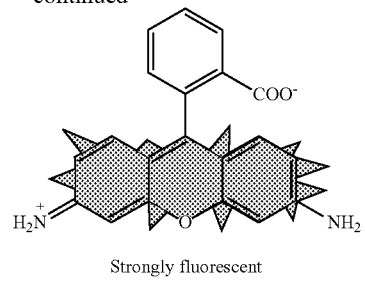

However, this fluorescent probe must be hydrolyzed at the two acyl groups for the generation of the open ring type strongly fluorescent diaminorhodamine, thus the fluorescence response consists of multiple steps, and therefore it has drawbacks such as poor real-time response property and poor suitability for quantification. In order to solve these problems, there has been desired development of a fluorescent probe that can cause a structural change from a closed ring structure to an open ring structure by a reaction at one reaction site to completely achieve off/on control of fluorescence.

PRIOR ART REFERENCES

Non-Patent Documents

Non-patent document 1: Biochemical Journal, 201, pp. 367-372, 1982
Non-patent document 2: Biochemistry, 38, pp. 13906-13911, 1999

SUMMARY OF THE INVENTION

Object to be Achieved by the Invention

An object of the present invention is to provide a fluorescent probe for measuring a protease. More specifically, the object of the present invention is to provide a fluorescent probe for measuring a protease utilizing the xanthene structure, which can cause a structural change from the closed ring structure to the open ring structure by a reaction at one reaction site to completely achieve off/on control of fluorescence, and has superior real-time response property and suitability for quantification.

Means for Achieving the Object

The inventors of the present invention conducted various researches to achieve the aforementioned object, and as a result, they found that a compound having the diaminorhodamine structure (for example, rhodamine 110) of which carboxyl group on the benzene ring was replaced with a hydroxy(lower alkyl) group such as hydroxymethyl group became a closed ring type nonfluorescent compound when the amino group at one side was acylated, and became an open ring type strongly fluorescent compound when that acyl group was removed. They also found that this structural change promptly occurred in a neutral pH solution to provide several hundreds times higher fluorescence intensity, and therefore this compound was successfully used as a fluorescent probe for measuring a protease. The present invention was accomplished on the basis of the aforementioned findings.

The present invention thus provides a compound represented by the following general formula (I):

[Formula 2]

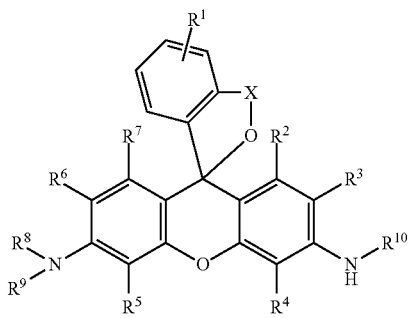

(I)

wherein $R^1$ represents hydrogen atom, or the same or different one to four substituents binding to the benzene ring; $R^2$, $R^3$, $R^4$, $R^5$, $R^6$ and $R^7$ independently represent hydrogen atom, hydroxyl group, an alkyl group, or a halogen atom; $R^8$ and $R^9$ independently represent hydrogen atom, or an alkyl group; X represents a $C_1$-$C_3$ alkylene group; and $R^{10}$ represents an acyl group, or a salt thereof.

According to a preferred embodiment of the aforementioned invention, there is provided the aforementioned compound or a salt thereof, wherein $R^1$, $R^2$, $R^3$, $R^4$, $R^5$, $R^6$, $R^7$, $R^8$ and $R^9$ are hydrogen atoms, X is methylene group, and $R^{10}$ is an alkylcarbonyl group, an alkyloxycarbonyl group an arylcarbonyl group, an aryloxycarbonyl group, an aralkylcarbonyl group, an alkylthiocarbonyl group, an alkylaminocarbonyl group, an arylthiocarbonyl group, an arylaminocarbonyl group, or an acyl residue derived from an amino acid (the acyl residue derived from an amino acid is a residue formed by removing the hydroxyl group from the carboxyl group of the amino acid). More preferably, there is provided the aforementioned compound or a salt thereof, wherein $R^1$, $R^2$, $R^3$, $R^4$, $R^5$, $R^6$, $R^7$, $R^8$ and $R^9$ are hydrogen atoms, X is methylene group, and $R^{10}$ is an acyl residue derived from an amino acid (the acyl residue derived from an amino acid is an acyl group corresponding to a partial structure remaining after removing the hydroxyl group from the carboxyl group of the amino acid).

From another aspect, the present invention provides a fluorescent probe for measuring a protease, which comprises a compound represented by the aforementioned general formula (I) or a salt thereof.

From a still further aspect, the present invention provides a method for measuring a protease, which comprises the following steps:

(1) the step of reacting a compound represented by the aforementioned general formula (I) or a salt thereof with a protease, and (2) the step of detecting a compound represented by the following general formula (II):

[Formula 3]

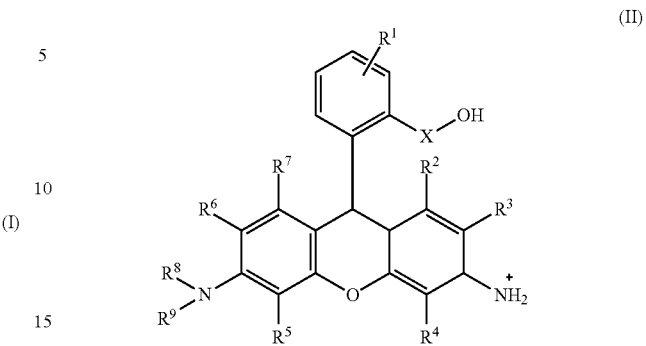

(II)

wherein $R^1$, $R^2$, $R^3$, $R^4$, $R^5$, $R^6$, $R^7$, $R^8$, $R^9$ and X have the same meanings as those defined above, or a salt thereof produced in the aforementioned step (1).

Effect of the Invention

The compound represented by the aforementioned general formula (I) provided by the present invention can cause a structural change from the closed ring structure to the open ring structure by a reaction at one reaction site to completely achieve off/on control of fluorescence, and can be used as a fluorescent probe for measuring a protease having superior real-time response property and suitability for quantification. Further, the fluorescent probe of the present invention utilizes the rhodamine structure, and accordingly, the compound represented by the general formula (II) or a salt thereof produced from the fluorescent probe taken up into cells by a reaction with a protease hardly leaks out of the cells. Therefore, the fluorescent probe of the present invention enables highly sensitive imaging in live cells or live tissues for a long period of time.

MODES FOR CARRYING OUT THE INVENTION

Figure 1:
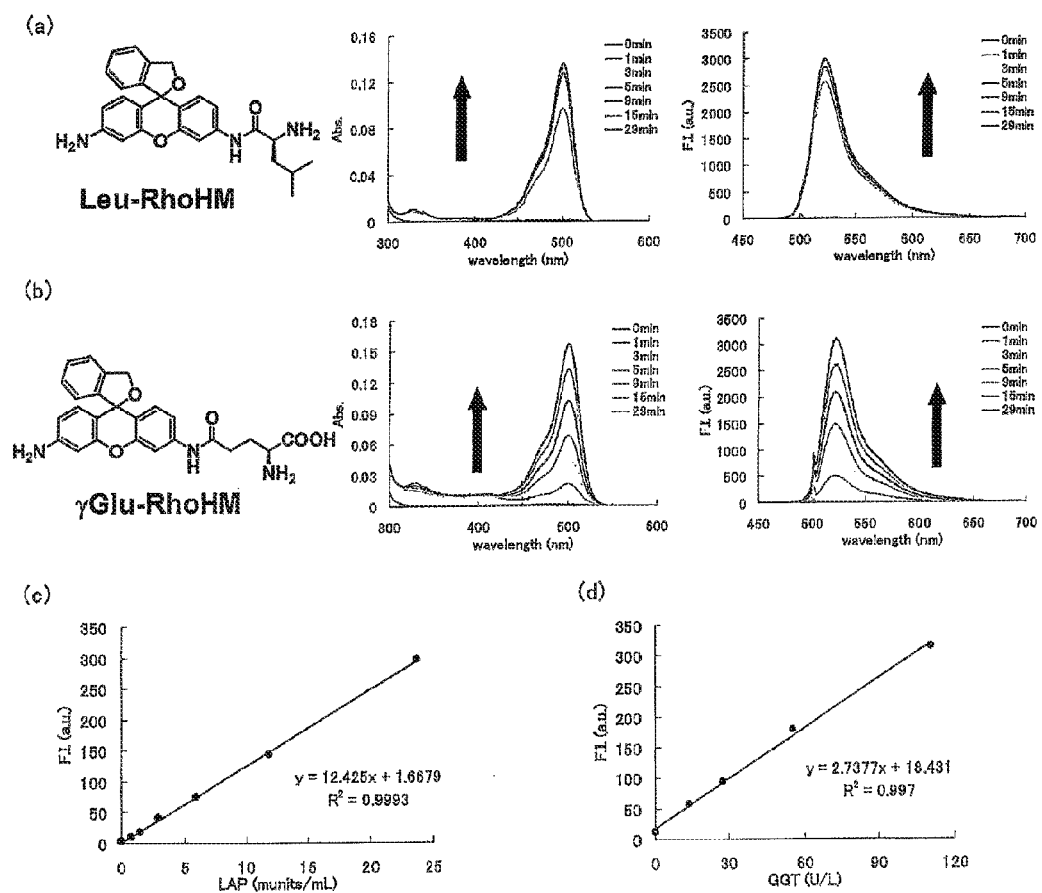
FIG. 1 shows reactivity of the compounds of the present invention with a protease. There are shown (a) changes of absorption and fluorescence spectra of Compound (2) (Leu-RhoHM) induced by the reaction with leucine aminopeptidase (LAP); (b) changes of absorption and fluorescence spectra of Compound (3) (γGlu-RhoHM) induced by the reaction with γ-glutamyl transpeptidase (GGT); (c) suitability of Leu-RhoHM for quantification by a reaction, and (d) suitability of γGlu-RhoHM for quantification by a reaction.

The alkyl group mentioned in this specification may be a linear, branched or cyclic alkyl group, or may be an alkyl group consisting of a combination thereof. Although the carbon number of the alkyl group is not particularly limited, the number may be, for example, about 1 to 6, preferably about 1 to 4. The alkyl group mentioned in this specification may have one or more arbitrary substituents. Examples of the substituent include, for example, an alkoxyl group, a halogen atom (the halogen atom may be any of fluorine atom, chlorine atom, bromine atom, and iodine atom), amino group, a monoor di-substituted amino group, a substituted silyl group, an acyl group, and the like, but the substituent is not limited to these examples. When the alkyl group has two or more substituents, they may be the same or different. The above descriptions are similarly applied to alkyl moieties of other substituents containing an alkyl moiety (for example, an alkyloxy group, an aralkyl group, and the like).

The aryl group mentioned in this specification may be either a monocyclic aryl group or a condensed polycyclic aryl group, and may contain one or more heteroatoms (for example, oxygen atom, nitrogen atom, sulfur atom and the like) as ring-constituting atoms. The aryl group mentioned in this specification may have one or more arbitrary substituents on the ring. Examples of the substituent include, for example, an alkoxyl group, a halogen atom, amino group, a mono- or di-substituted amino group, a substituted silyl group, an acyl group, and the like, but the substituent is not limited to these examples. When the aryl group has two or more substituents, they may be the same or different. The above descriptions are similarly applied to aryl moieties of other substituents containing an aryl moiety (for example, an aryloxy group, an aralkyl group, and the like).

$R^1$ represents hydrogen atom, or one to four substituents binding to the benzene ring. Examples of the substituent include, for example, an alkyl group, an alkoxyl group, a halogen atom, amino group, a mono- or di-substituted amino group, a substituted silyl group, an acyl group, and the like, but the substituent is not limited to these examples. When there are two or more substituents on the benzene ring, they may be the same or different. As $R^1$, hydrogen atom is preferred.

$R^2$, $R^3$, $R^4$, $R^5$, $R^6$ and $R^7$ independently represent hydrogen atom, hydroxyl group, an alkyl group, or a halogen atom. It is preferred that $R^2$ and $R^7$ are hydrogen atoms It is also preferred that $R^3$, $R^4$, $R^5$ and $R^6$ are hydrogen atoms. It is more preferred that all of $R^2$, $R^3$, $R^4$, $R^5$, $R^6$ and $R^7$ are hydrogen atoms.

$R^8$ and $R^9$ independently represent hydrogen atom or an alkyl group. When both $R^8$ and $R^9$ represent an alkyl group, they may be the same or different. For example, it is preferred that both $R^8$ and $R^9$ are hydrogen atoms, or $R^8$ is an alkyl group and $R^9$ is hydrogen atom, and it is more preferred that both $R^8$ and $R^9$ are hydrogen atoms.

X represents a $C_1$-$C_3$ alkylene group. The alkylene groups may be either a linear alkylene group or a branched alkylene group. For example, in addition to methylene group (—$CH_2$—), ethylene group (—$CH_2$—$CH_2$—), and propylene group (—$CH_2$—$CH_2$—$CH_2$—), —$CH(CH_3)$—, —$CH_2$—$CH(CH_3)$—, —$CH(CH_2CH_3)$—, and the like can also be used as branched alkylene groups. Among them, methylene group and ethylene group are preferred, and methylene group is more preferred.

$R^{10}$ represents an acyl group. The acyl group mentioned in this specification may be either an aliphatic acyl group or an aromatic acyl group, or may be an aliphatic acyl group having an aromatic group as a substituent. The acyl group may contain one or two or more heteroatoms. Examples of the acyl group include, for example, such acyl groups as an alkylcarbonyl group (acetyl group and the like), an alkyloxycarbonyl group (acetoxycarbonyl group and the like), an arylcarbonyl group (benzoyl group and the like), an aryloxycarbonyl group (phenyloxycarbonyl group and the like), an aralkylcarbonyl group (benzylcarbonyl group and the like), an alkylthiocarbonyl group (methylthiocarbonyl group and the like), an alkylaminocarbonyl group (methylaminocarbonyl group and the like), an arylthiocarbonyl group (phenylthiocarbonyl group and the like), and an arylaminocarbonyl group (phenylaminocarbonyl group and the like), but the acyl group is not limited to these examples. These acyl groups may have one or more arbitrary substituents. Examples of the substituent include an alkoxyl group, a halogen atom, amino group, a mono- or di-substituted amino group, a substituted silyl group, an acyl group, and the like, but the substituent is not limited to these examples. When the acyl group has two or more substituents, they may be the same or different.

Examples of the acyl group represented by $R^{10}$ also include an acyl group corresponding to a partial structure of an amino acid remaining after removing the hydroxyl group from the carboxyl group of the amino acid (herein referred to as "acyl residue derived from an amino acid"), and the like. As the amino acid, an arbitrary compound may be used so long as a compound having both amino group and carboxyl group is chosen, and the amino acid may be any of a neutral amino acid, a basic amino acid, and an acidic amino acid. There can preferably be used amino acids that themselves function as transmitter substances such as neurotransmitters, as well as amino acids that are constituents of such polypeptide compounds as biologically active peptides (including oligopeptides besides dipeptides, tripeptides and tetrapeptides) and proteins, and the amino acid may be, for example, an α-amino acid, β-amino acid, γamino acid, or the like. It is preferable to use an optically active amino acid as the amino acid. For example, although either a D- or L-amino acid may be used as the α-amino acid, it may be preferable to choose an optically active amino acid that functions in a living body. More specifically, as the amino acid, there can also be used, for example, 20 kinds of the L-amino acids constituting proteins, as well as selenocysteine, pyrrolysine, cystine, hydroxyproline, hydroxylysine, tyroxine, O-phosphoserine, desmosine, β-alanine, sarcosine, ornithine, creatine, γ-aminobutyric acid, opaine, and the like.

The compound represented by the aforementioned general formula (I) may exist as a salt. Examples of the salt include a base addition salt, an acid addition salt, an amino acid salt, and the like. Examples of the base addition salt include, for example, metal salts such as sodium salts, potassium salts, calcium salts, and magnesium salts; ammonium salts, and organic amine salts such as triethylamine salts, piperidine salts, and morpholine salts. Examples of the acid addition salt include, for example, mineral acid salts such as hydrochlorides, sulfates, and nitrates, and organic acid salts such as methanesulfonates, p-toluenesulfonates, citrates, and oxalates. Examples of the amino acid salt include glycine salts and the like. However, salts of the compounds of the present invention are not limited to these examples.

The compound of the present invention represented by the general formula (I) may have one or two or more asymmetric carbons depending on the type of the substituent, and stereoisomers such as optical isomers or diastereoisomers may exist. These stereoisomers in pure forms, arbitrary mixtures of these stereoisomers, racemates and the like all fall within the scope of the present invention.

The compound represented by the general formula (I) or a salt thereof may exist as a hydrate or a solvate, and any of these substances fall within the scope of the present invention. The type of solvent that forms the solvate is not particularly limited. For example, such solvents as ethanol, acetone and isopropanol can be exemplified.

The compound of the present invention represented by the general formula (I) can be readily prepared from, for example, a xanthene compound having amino groups at the 3- and 6-positions and 2-carboxyphenyl group or an 2-alkoxycarbonylphenyl group at the 9-position or the like used as the starting material by, for example, converting the 2-carboxyphenyl group or 2-alkoxycarbonylphenyl group at the 9-position into a hydroxyalkyl group and then acylating the amino group at the 3-position. As the 3,6-diaminoxanthene compound usable as the starting material, there can be exemplified, for example, rhodamine 110, rhodamine 123, and the like, which are all commercially available, but the 3,6-diaminoxanthene compound is not limited to these examples, and an appropriate xanthene compound can be chosen according to the structure of the objective compound. Preparation methods for typical compounds among the compounds of the present invention represented by the general formula (I) are specifically described in the examples mentioned in this specification, and accordingly, those skilled in the art can readily prepare an arbitrary compound among the compounds of the present invention represented by the general formula (I), by referring to the disclosures of the present specification, and appropriately choosing starting materials, reagents, reaction conditions, and the like, as required.

The compound of the present invention represented by the general formula (I) can be used as a fluorescent probe for measuring a protease. The compound of the present invention having a closed ring structure is substantially non-fluorescent in the neutral pH condition (for example, in the range of pH 5 to 9). However, when the acyl group represented by $R^{10}$ is hydrolyzed by a protease, the compound promptly becomes a tautomer having an open ring structure to give a strongly fluorescent compound represented by the general formula (II). For example, the compound represented by the general formula (I) or a salt thereof emits almost no fluorescence when irradiated with an excitation light of about 500 nm in the neutral region, whilst the compound represented by the general formula (II) has a property of emitting extremely strong fluorescence (for example, emission: 524 nm) under the same conditions. Therefore, use of the compound of the present invention as a fluorescent probe for measuring a protease enables measurement of presence of a protease on the basis of change of fluorescence intensity.

The method for measuring a protease generally comprises the following steps: (1) the step of reacting a compound represented by the aforementioned general formula (I) or a salt thereof with a protease; and (2) the step of detecting a compound represented by the following general formula (II) or a salt thereof produced in the aforementioned step (1). By allowing a compound represented by the general formula (I) to be taken up into living tissues or cells and react with a protease to produce a fluorescent compound represented by the general formula (II), and measuring fluorescence of this compound, the protease in the living tissues or cells can be measured.

Type of the protease is not particularly limited, so long as a protease is chosen that can hydrolyze the acyl group represented by $R^{10}$ in the compound represented by the aforementioned general formula (I). For example, the protease may be either an endoprotease or an exoprotease, and may be a protease classified into proteinase or peptidase. For example, in order to measure a protease which uses a specific amino acid as a substrate, on acyl residue derived from the aforementioned specific amino acid can be used as the acyl group represented by $R^{10}$, and a particular protease can be specifically measured by using the compound designed as described above. From such a point of view, it is preferable to use an acyl residue derived from an amino acid hydrolysable with a protease as the acyl group represented by $R^{10}$. For example, it is preferable to use acyl residues derived from 20 kinds of the L-amino acids constituting proteins, selenocysteine, pyrrolysine, cystine, hydroxyproline, hydroxylysine, tyroxine, O-phosphoserine, desmosine, β-alanine, sarcosine, ornithine, creatine, γ-aminobutyric acid, opaine, and the like.

In this specification, the term "measurement" should be construed in its broadest sense, including measurements for various purposes, such as detection, quantification, and qualification. Measurement of a protease by the method of the present invention can be performed under a neutral condition, for example, in the range of pH 5.0 to 9.0, preferably in the range of pH 6.0 to 8.0, more preferably in the range of pH 6.8 to 7.6.

The compound of the present invention represented by the general formula (I) is easily taken up into cells, and the open ring type compound represented by the general formula (II) generated from the compound represented by the general formula (I) can be retained in the cells over a long period of time without being leaked out of the cells. Therefore, the compound has a superior characteristic that it enables measurement of a protease in cells over a long period of time. In particular, the compound of the present invention represented by the general formula (II) has a property of emitting extremely strong fluorescence, and has extremely superior retentivity in cells, and therefore the compound has a characteristic feature that it enables highly sensitive measurement of a trace amount of a protease existing in cells over a long period of time.

Although the compound represented by the aforementioned formula (I) or a salt thereof per se may be used as the fluorescent probe for measuring a protease of the present invention, the compound may be used as a composition by mixing the compound with additives generally used for reagent preparation, if necessary. For example, as additives for use of reagents under a physiological condition, such additives as dissolving aids, pH adjusters, buffers, and isotonic agents can be used, and amounts of these additives can suitably be chosen by those skilled in the art. Such a composition may be provided as those in appropriate forms, for example, powdery mixtures, lyophilized products, granules, tablets, solutions and the like.

EXAMPLES

The present invention will be more specifically explained with reference to examples. However, the scope of the present invention is not limited to the following examples.

Example 1

Compounds (2) to (7) were prepared according to the following schemes.

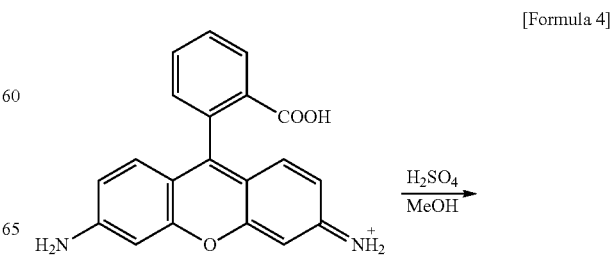

[Formula 4]

9
-continued
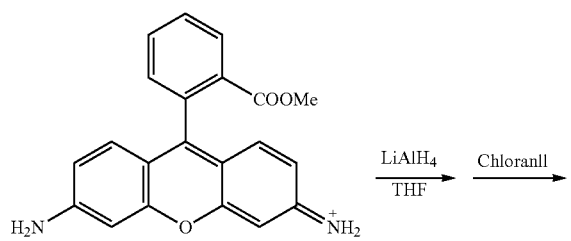
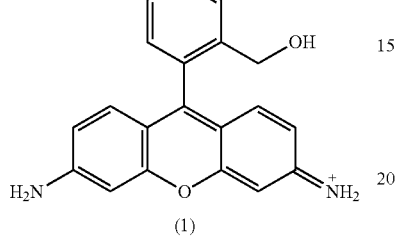
(1)
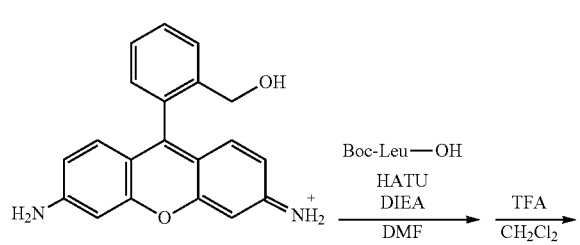
(2)
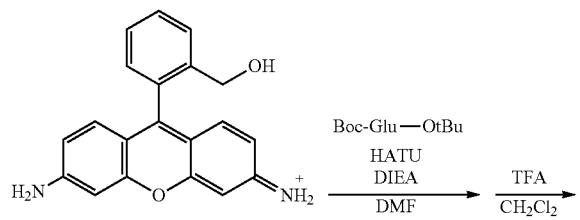
(3)
10
-continued
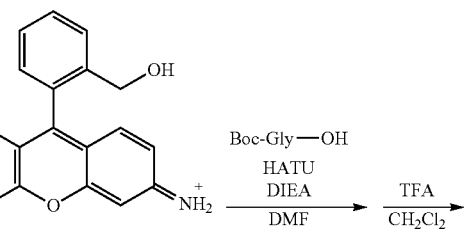
(4)
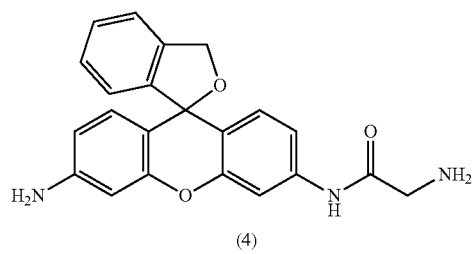
(5)
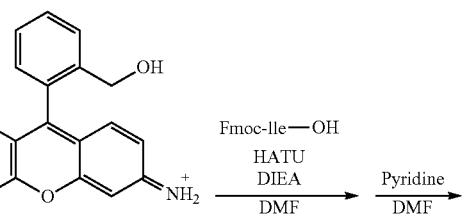
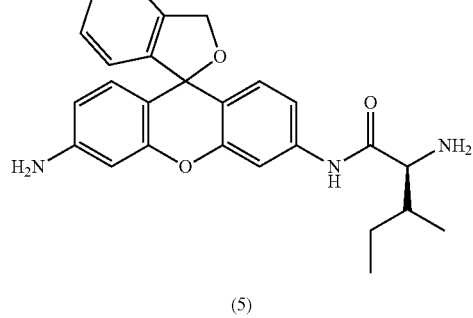
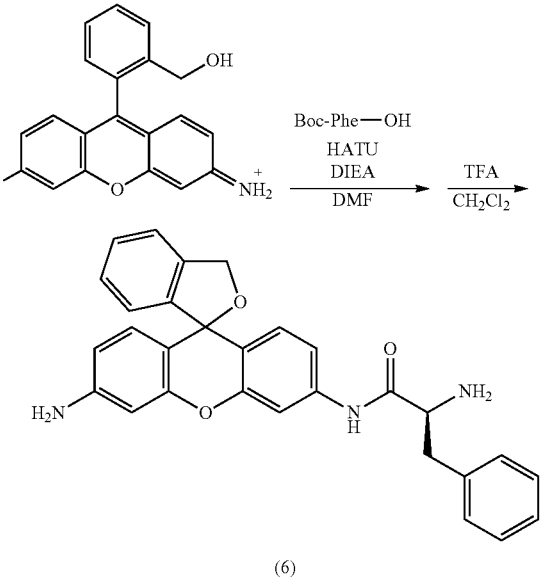
(6)

-continued

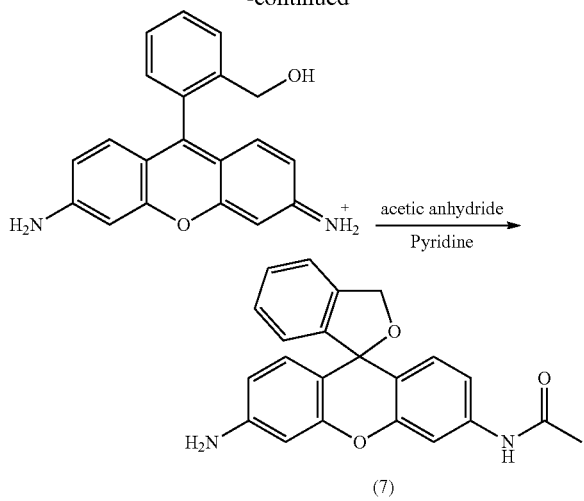

(a) Synthesis of Compound (1) (RhoHM)

Rhodamine 110 (285 mg, 0.8 mmol, 1 eq.) was dissolved in methanol (10 mL), the solution was added with sulfuric acid, and the mixture was stirred at 80° C. for 10 hours under an argon atmosphere. The reaction solvent was removed under reduced pressure, and the residue was washed with saturated aqueous sodium hydrogencarbonate and water. The resulting solid was dissolved in tetrahydrofuran (THF, 10 mL), the solution was added with a 5 M sodium methoxide solution (in methanol, 400 μL, 0.8 mmol, 1 eq.) at 0° C. under an argon atmosphere, and the mixture was stirred for 10 minutes. Then, the mixture was added with lithium aluminum hydride (333 mg, 8 mmol, 10 eq.), and the mixture was stirred for 3 hours. The reaction mixture was added with saturated aqueous ammonium chloride (5 mL), the solvent was removed under reduced pressure, and the resulting solid was extracted with dichloromethane and a saturated aqueous solution of tartaric acid tetrahydrate potassium and sodium salt. The organic layer was added with sodium sulfate, and filtered, and then the solvent was removed to obtain solid. The resulting solid was dissolved in dichloromethane, the solution was added with chloranil (196 mg, 1 mmol, 1 eq.), and the mixture was stirred at room temperature for 30 minutes. The solvent was removed under reduced pressure, and the residue was purified by silica gel chromatography (dichloromethane/methanol=10:1) to obtain the objective compound (104 mg, 41%).

$^1$H NMR (300 MHz, CD$_3$OD): δ 7.64 (d, 1H, J=7.7 Hz), 7.56 (t, 1H, J=7.6 Hz), 7.44 (t, 1H, J=7.5 Hz), 7.17 (d, 1H, J=7.5 Hz), 7.03-7.00 (m, 2H), 6.71-6.74 (m, 4H), 4.23 (s, 2H)

$^{13}$C NMR (400 MHz, CD$_3$OD): δ 161.5, 159.9, 159.6, 141.0, 133.4, 132.2, 131.3, 130.3, 129.5, 128.8, 118.0, 115.0, 98.4, 62.8

HRMS (ESI+) Calcd for [M+H]+, 317.12900. Found, 317.12862 (−0.38 mmu)

(b) Synthesis of Compound (2) (Leu-RhoHM)

Compound (1) (17.7 mg, 0.05 mmol, 1 eq.), HATU (42.4 mg, 0.11 mmol, 2 eq.) and N,N-diisopropylethylamine (19.5 μL, 0.11 mmol, 2 eq.) were dissolved in dimethylformamide (DMF, 2 mL), and the solution was stirred at 0° C. for 10 minutes under an argon atmosphere. Then, the reaction mixture was added with DMF (0.5 mL) dissolving Boc-Leu-OH (13.9 mg, 0.05 mmol, 1 eq.), and the mixture was stirred for 15 hours. The reaction solvent was removed under reduced pressure, then the resulting solid was dissolved in dichloromethane (2 mL) and trifluoroacetic acid (TFA, 2 mL), and the solution was stirred for 30 minutes. The solvent was removed, and the residue was purified by HPLC (eluent A:H$_2$O containing 0.1% TFA, eluent B:80% of CH$_3$CN and 20% H$_2$O containing 0.1% TFA, A/B=80/20 to 0/100 for 40 minutes) to obtain the objective compound (5.7 mg, 24%).

$^1$H NMR (300 MHz, CD$_3$OD): δ 7.55-7.54 (m, 1H), 7.33-7.27 (m, 2H), 7.18 (t, 1H, J=7.3 Hz), 7.03-7.01 (m, 1H), 6.76-6.72 (m, 2H), 6.55 (d, 1H, J=8.4 Hz), 6.41 (d, 1H, J=2.0 Hz), 6.33-6.30 (m, 1H), 5.15 (s, 2H), 3.58-3.57 (m, 1H), 1.62-1.43 (m, 3H), 0.89 (m, 6H)

$^{13}$C NMR (400 MHz, CD$_3$OD): δ170.6, 164.8, 161.8, 160.5, 156.7, 147.5, 141.3, 135.0, 132.0, 131.7, 130.5, 129.9, 129.0, 121.8, 119.8, 119.4, 119.1, 116.7, 107.7, 98.6, 63.2, 54.0, 41.5, 23.3, 21.7

HRMS (ESI+) Calcd for [M+H]+, 430.21307. Found, 430.21210 (−0.96 mmu)

(c) By using Boc-Glu-OtBu, Boc-Gly-OH, Fmoc-Ile-OH, Boc-Phe-OH and acetic anhydride, Compound (3) (γGlu-RhoHM), Compound (4) (Gly-RhoHM), Compound (5) (Ile-RhoHM), Compound (6) (Phe-RhoHM) and Compound (7) (Acetyl-RhoHM) were obtained, respectively, in the same manner as that of (b) mentioned above.

Compound (3)

$^1$H NMR (400 MHz, CD$_3$OD): δ 8.39 (s, 1H), 7.62-7.61 (m, 2H), 7.50-7.47 (m, 1H), 7.39 (d, 1H, J=7.8 Hz), 7.24-7.22 (m, 3H), 6.94 (d, 1H, J=8.3 Hz), 6.86 (s, 1H), 4.25 (s, 2H), 3.96 (t, 1H, J=6.3 Hz), 2.71-2.69 (m, 2H), 2.30-2.27 (m, 2H)

$^{13}$C NMR (400 MHz, CD$_3$OD): δ173.4, 171.8, 164.5, 163.1, 160.7, 157.1, 148.7, 141.2, 134.9, 131.9, 131.7, 130.5, 129.8, 129.0, 121.4, 119.4, 118.5, 106.9, 98.5, 63.1, 53.5, 33.4, 26.6

HRMS (ESI+) Calcd for [M+H]+, 446.17160. Found, 446.17195 (+0.36 mmu)

Compound (4)

$^1$H NMR (300 MHz, CD$_3$OD): δ 8.45 (s, 1H), 7.72-7.69 (m, 2H), 7.59-7.56 (m, 1H), 7.50 (d, 1H), 7.38-7.34 (m, 3H), 7.05 (d, 1H), 6.96 (s, 1H), 4.35 (s, 2H), 3.98 (s, 2H)

$^{13}$C NMR (100 MHz, CD$_3$OD): δ 167.1, 164.8, 161.8, 160.6, 156.9, 147.6, 141.2, 134.9, 132.1, 131.7, 130.5, 129.9, 129.0, 121.7, 119.7, 119.2, 118.9, 107.3, 98.6, 63.2, 42.7, 42.2

HRMS (ESI+) Calcd for [M+H]+, 374.15047. Found, 374.14897 (−1.50 mmu)

Compound (5)

$^1$H NMR (300 MHz, CD$_3$OD): δ 8.49 (s, 1H), 7.72-7.69 (m, 2H), 7.59-7.53 (m, 2H), 7.42-7.34 (m, 3H), 7.05 (d, 1H), 6.97 (s, 1H), 4.35 (s, 2H), 3.97-3.95 (m, 1H), 2.08-2.03 (m, 1H), 1.32-1.29 (m, 2H), 1.12 (d, 3H), 0.99 (t, 3H)

HRMS (ESI+) Calcd for [M+H]+, 430.21307. Found, 430.21296 (−0.11 mmu)

Compound (6)

$^1$H NMR (300 MHz, CD$_3$OD): δ 8.42 (s, 1H), 7.75-7.71 (m, 2H), 7.58-7.55 (m, 2H), 7.44-7.41 (m, 3H), 7.08-6.97 (m, 2H), 6.84 (m, 2H), 6.70 (d, 1H, J=8.1 Hz), 6.56-6.48 (m, 2H), 4.30 (s, 2H), 4.16 (t, 1H, J=7.0 Hz), 3.55-3.53 (m, 1H), 3.27-3.25 (m, 1H)

HRMS (ESI+) Calcd for [M+H]+, 464.19742. Found, 464.19652 (−0.89 mmu)

Compound (7)

$^1$H NMR (300 MHz, CD$_3$OD): δ 7.63 (s, 1H), 7.44-7.42 (m, 2H), 7.31 (t, 1H, J=7.2 Hz), 7.10 (d, 1H, J=8.5 Hz), 6.86-6.83 (m, 2H), 6.67 (d, 1H, J8.4 Hz), 6.54 (s, 1H), 6.45 (d, 1H, J=8.4 Hz), 5.28 (s, 2H), 2.16 (s, 3H)

$^{13}$C NMR (400 MHz, CD$_3$OD): δ 172.5, 164.5, 161.7, 160.7, 157.2, 148.9, 141.2, 134.8, 131.8, 131.7, 130.5, 129.8, 129.0, 121.4, 119.3, 118.4, 106.8, 98.5, 63.1, 24.3

HRMS (ESI+) Calcd for [M+H]+, 359.13957. Found, 359.13904 (−0.53 mmu)

Example 2

Compound (2) (Leu-RhoHM) and Compound (3) (γGlu-RhoHM) formed by bonding acyl residues derived from leucine and glutamic acid to one amino group of Compound (1) (RhoHM), respectively, were each dissolved in a neutral phosphate buffer, and reacted with a protease (leucine aminopeptidase, LAP, porcine kidney, SIGMA L5006-25UN) and γ-glutamyl transpeptidase (GGT, equine kidney, SIGMA G9270-100UN). Specifically, 3 μL of a 5 μM solution of each compound in dimethyl sulfoxide (DMSO) was dissolved in 3 mL of a 0.1 M sodium phosphate buffer (pH 7.4) at a final concentration of 5 μM, and each of LAP (0.15 U) and GGT (1.1 U) was added to the solution to allow an enzymatic reaction at 37° C. The excitation wavelength was 501 nm. As a result, both gave a compound having the open ring structure by hydrolysis of the acyl group with the protease, and as a result, prompt marked increase of absorption and fluorescence intensity was observed (FIG. 1).

Further, each of the DMSO solutions of both compounds (5 mM) in a volume of 3 μL was dissolved in 3 mL of a 0.1 M sodium phosphate buffer (pH 7.4) at a final concentration of 5 μM, and the enzymatic reaction was performed at 37° C. The values of fluorescence intensity observed with each amount of the enzymes 1 minute (Leu-RhoHM) or 9 minutes (γGlu-RhoHM) after the addition of the enzyme were plotted. The excitation wavelength was 501 nm, and the fluorescence emission wavelength was 524 nm. Both compounds gave linear increase of fluorescence intensity in a dependent manner with the added protease amount (FIG. 1).

Example 3

Figure 2:
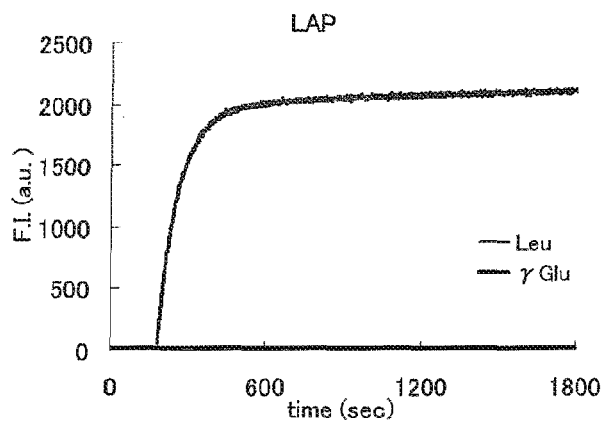
FIG. 2 shows reactivity of LAP with Compound (2) (Leu-RhoHM) and Compound (3) (γGlu-RhoHM).
Figure 3:
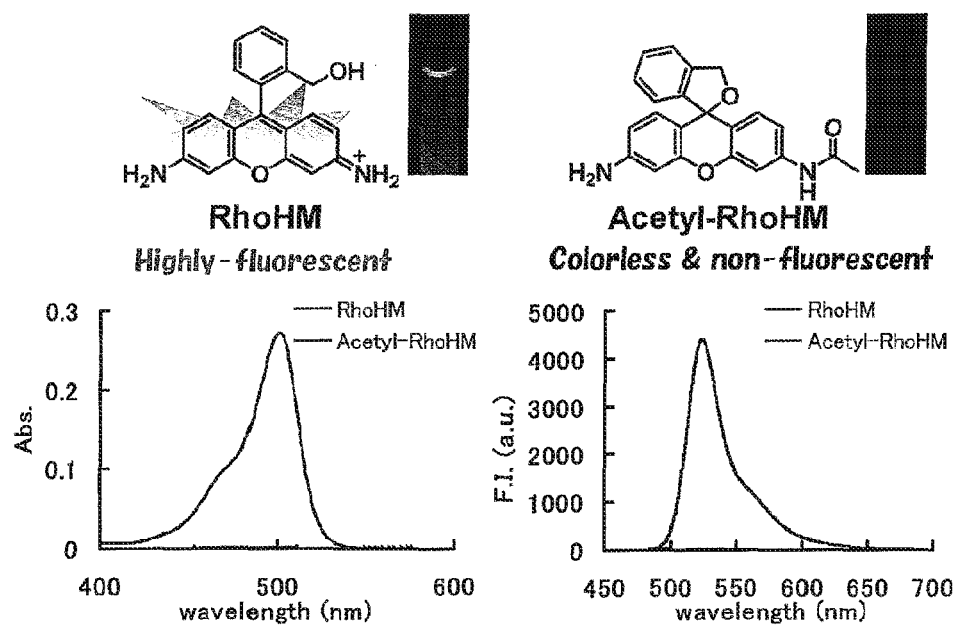
FIG. 3 shows spectroscopic characteristics of Compound (7) (Acetyl-RhoHM) and Compound (1) (RhoHM) at pH 7.4 (in water).

Enzyme specificity of Compounds (2) and (3) was examined. Each of the DMSO solutions (3 μL) was dissolved in 3 mL of a 0.1 M sodium phosphate buffer (pH 7.4) at a final concentration of 5 μM, and LAP (0.4 U) was added to the solution to perform the enzymatic reaction at 37° C. As a result, marked increase of fluorescence intensity was observed after the reaction of Compound (2) (Leu-RhoHM) with LAP, whereas increase of fluorescence intensity was not observed after the reaction of Compound (3) (γGlu-RhoHM) with LAP (FIG. 2). On the other hand, Compound (3) reacted with GGT to give marked fluorescence intensity (Example 2), and therefore it was considered that GGT was specifically detected with γGlu-RhoHM.

What is claimed is:

1. A compound represented by the following general formula (I):

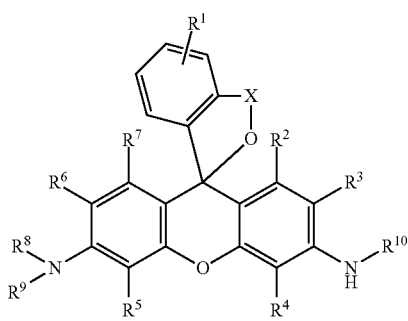

(I)

wherein $R^1$ represents hydrogen atom, or the same or different one to four substituents binding to the benzene ring; $R^2$, $R^3$, $R^4$, $R^5$, $R^6$ and $R^7$ independently represent hydrogen atom, hydroxyl group, an alkyl group, or a halogen atom; $R^8$ and $R^9$ independently represent hydrogen atom, or an alkyl group; X represents a $C_1$-$C_3$ alkylene group; and $R^{10}$ represents an acyl group residue derived from an amino acid or a peptide, or a salt thereof.

2. The compound or the salt thereof according to claim 1, wherein $R^1$, $R^2$, $R^3$, $R^4$, $R^5$, $R^6$, $R^7$, $R^8$ and $R^9$ are hydrogen atoms, X is methylene group, and $R^{10}$ is an acyl residue derived from an amino acid.

3. A fluorescent probe for measuring a protease, which comprises the compound represented by the general formula (I) or the salt thereof according to claim 1.

4. A method for measuring a protease, which comprises the following steps:
   (1) the step of reacting the compound represented by the aforementioned general formula (I) or the salt thereof according to claim 1 with a protease, and
   (2) the step of detecting a compound represented by the following general formula (II):

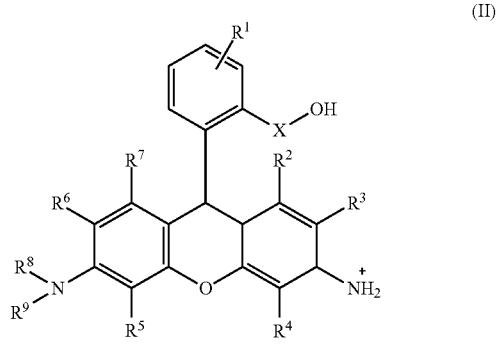

(II)

wherein $R^1$, $R^2$, $R^3$, $R^4$, $R^5$, $R^6$, $R^7$, $R^8$, $R^9$ and X have the same meanings as those defined above, or a salt thereof produced in the step (1).

5. A fluorescent probe for measuring a protease, which comprises the compound represented by the general formula (I) or the salt thereof according to claim 2.

6. A method for measuring a protease, which comprises the following steps:
   (1) the step of reacting the compound represented by the aforementioned general formula (I) or the salt thereof according to claim 2 with a protease, and
   (2) the step of detecting a compound represented by the following general formula (II):

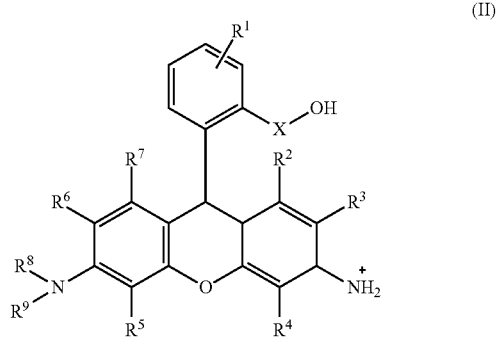

(II)

wherein $R^1$, $R^2$, $R^3$, $R^4$, $R^5$, $R^6$, $R^7$, $R^8$, $R^9$ and X have the same meanings as those defined above, or a salt thereof produced in the step (1).

* * * * *

UNITED STATES PATENT AND TRADEMARK OFFICE
CERTIFICATE OF CORRECTION

| | |
|---|---|
| PATENT NO. | : 8,461,358 B2 |
| APPLICATION NO. | : 13/201537 |
| DATED | : June 11, 2013 |
| INVENTOR(S) | : T. Nagano et al. |

It is certified that error appears in the above-identified patent and that said Letters Patent is hereby corrected as shown below:

On the Title Page; (73) Assignee, change "Toyko (JP)" to -- Tokyo (JP) --.

On the Title Page; References Cited; U.S. Patent Documents, change "4,557,862 A   12/1985   Mnagel et al." to -- 4,557,862 A   12/1985   Mangel et al. --.

Signed and Sealed this
Seventh Day of January, 2014

Margaret A. Focarino
*Commissioner for Patents of the United States Patent and Trademark Office*